United States Patent [19]

Ciganek

[11] Patent Number: 4,477,456

[45] Date of Patent: Oct. 16, 1984

[54] OCTAHYDRO-4A,7-ETHANO- AND -ETHENO-BENZOFURO[3,2-E]ISOQUINO-LINE DERIVATIVES HAVING ANALGESIC, NARCOTIC ANTAGONIST AND ANOREXIGENIC PROPERTIES

[75] Inventor: Engelbert Ciganek, Kennett Square, Pa.

[73] Assignee: E. I. Du Pont de Nemours and Company, Wilmington, Del.

[21] Appl. No.: 370,137

[22] Filed: Apr. 22, 1982

Related U.S. Application Data

[63] Continuation-in-part of Ser. No. 280,130, Jul. 2, 1981, abandoned.

[51] Int. Cl.³ .................... A61K 31/47; C07D 491/08
[52] U.S. Cl. ...................................... 424/258; 546/44; 546/45; 546/46
[58] Field of Search ............................ 546/44, 45, 46; 424/258

[56] References Cited

U.S. PATENT DOCUMENTS

| | | | |
|---|---|---|---|
| 3,318,885 | 5/1967 | Brown et al. | 546/45 X |
| 3,318,886 | 5/1967 | Brown et al. | 546/45 X |
| 3,474,101 | 10/1969 | Bentley | 546/39 |
| 3,488,354 | 1/1970 | Brown et al. | 546/45 X |
| 4,243,668 | 1/1981 | Ciganek | 424/258 |
| 4,260,761 | 4/1981 | Ciganek | 546/66 |

FOREIGN PATENT DOCUMENTS 9780 4/1980 European Pat. Off. ............ 424/258

OTHER PUBLICATIONS

L. W. Lewis in M. C. Braude, et al., (Eds.), *Narcotic Antagonists (Adv. Biochem. Psychopharmacol.)* (N.Y.: Raven Press, 1974), vol. 8, pp. 123–136.
K. W. Bentley in R. H. F. Manske, (ed.), *The Alkaloids* (N.Y.: Academic Press, 1977), vol. 13, pp. 75–80.
Crabbendam, et al., J. Royal Netherlands Chem. Soc., 100, (7–8), pp. 293–294 (1981).
Bentley, et al., J. Am. Chem. Soc., vol. 89(13), pp. 3281–3292 (1967).
Schultz, et al., J. Am. Chem. Soc., vol. 100(7), pp. 2150–2162 (1978).
Ciganek, J. Am. Chem. Soc., vol. 103, pp. 6261–6262 (10/07/81).
Moos, et al., Chemical Abstracts, vol. 96, 6920d (1982).
Martin, et al., J. Pharmacol. Exp. Ther., vol. 197, No. 3, pp. 517–532, (1976).

*Primary Examiner*—Donald G. Daus
*Assistant Examiner*—Diana G. Rivers

[57] ABSTRACT

Novel bridged benzofuroisoquinoline compounds having analgesic, narcotic antagonist and anorexigenic properties.

11 Claims, No Drawings

OCTAHYDRO-4A,7-ETHANO- AND -ETHENO-BENZOFURO[3,2-E]ISOQUINOLINE DERIVATIVES HAVING ANALGESIC, NARCOTIC ANTAGONIST AND ANOREXIGENIC PROPERTIES

RELATED APPLICATION

This application is a continuation-in-part of my copending application U.S. Ser. No. 280,130, filed July 2, 1981, now abandoned.

FIELD OF THE INVENTION

This invention relates to bridged benzofuroisoquinoline compounds, processes for their manufacture, and their use as analgesics, as narcotic antagonists, and as anorexia-inducing agents.

BACKGROUND OF THE INVENTION

Pain is an essential sensation in the protection of the body from damaging influences. However, because said pain frequently persists after it has played its essential role, it becomes desirable to treat the subject to reduce the sensation of pain. Drugs which are effective to reduce pain, i.e., analgesics, act by different mechanisms. There are:

(1) drugs which reduce pain by treating its source, e.g., glyceryl trinitrate in the treatment of angina;

(2) drugs of the nonnarcotic, nonsteroidal, antiinflammatory, antipyretic type, which may act in part peripherally to relieve pain by inhibition of prostaglandin synthetase, or by an antiinflammatory effect, e.g., aspirin or acetaminophen; and (3) drugs which act mainly on the perception of pain by the brain, e.g., morphine and certain morphine derivatives.

Analgesics are also classified by their mode of use. Thus, in general, when the intensity of pain is mild to moderate, a simple (mild) analgesic is given. However, when the pain is moderate to severe, a strong analgesic is indicated.

The most important strong analgesic compounds include opium preparations, purified alkaloids (e.g., morphine), semi-synthetic morphine modifications (e.g., oxymorphone) and various synthetic morphine-like compounds (phenyl piperidine structures). In addition to morphine itself, the most widely used analgesics are oxycodone, oxymorphone, levorphanol, methadone and pethidine (meperidine). Morphine is the standard to which strong analgesics are compared.

Morphine, which acts on the central nervous system to repress pain perception, causes drowsiness, euphoria (and sometimes dysphoria) and depresses respiration. Morphine and the many drugs related thereto incur high degrees of dependence. This is, of course, no problem in short-term treatment of pain, but becomes a serious problem in treatment of chronic pain.

Because the narcotic-like analgesics also act to depress the respiratory system, overdosage of such compounds is extremely dangerous. It has been found, however, that several N-allyl derivatives, including the N-allyl derivatives of morphine (nalorphine), levorphanol (levallorphan) and oxymorphone (naloxone), effectively antagonize overdoses of the opiate analgesics. Two of these, nalorphine and levallorphan, have some analgesic effects by themselves, but naloxone is a pure antagonist having no intrinsic analgesic activity. Naloxone is a versatile material which is capable of reversing the action (including the analgesia) of larger doses of a narcotic and which also antagonizes the emetic effect of meperidine. Though such antagonists have been shown to be effective in antagonizing overdoses of narcotics, they have not been shown to be effective in administration with narcotics to reverse respiratory depression without also reversing the desirable analgesic effects of the opiate. Thus, it would be highly desirable to obtain a compound which combines significant narcotic analgesic activity as well as narcotic antagonistic activity in the same molecule.

Since Lasagna and Beecher (Lasagna, L. and Beecher, H. K., "The Analgesic Effectiveness of Nalorphine and Nalorphine-Morphine Combinations", in *Man. J. Pharmacol. Exp. Ther.*, 112, pp. 356–363, 1954) reported that the narcotic antagonist nalorphine also has analgetic properties in man, a wide-ranging search for agonist/antagonist compounds possessing both analgetic and narcotic antagonist properties has led to the discovery of a number of clinically useful agents (e.g., pentazocine, cyclazocine, butorphanol, nalbuphine) which have a lower abuse potential than pure narcotic agonist compounds. Generally, but with some exceptions, substitution of $C_n$ homologues, wherein $n \geq 2$, for the N-methyl group in morphine, codeine, and other narcotics produces compounds which possess an antagonist component with or without loss of analgetic potency; thus within a single chemical series there may be compounds possessing pure agonist, combined agonist/antagonist, and pure antagonist properties (Jaffe, J. H. and Martin, W. R., "Narcotic Analgesics and Antagonists", in *The Pharmacological Basis of Therapeutics*, L. S. Goodman and A. Gilman (Eds.), MacMillan Publishing Co., Inc., New York, 1975, p. 272).

Another serious problem for which help is often sought is obesity. It can lead to a number of serious side-effects, not the least of which is an increased risk of cardiovascular disease. A number of appetite supressants are currently available for the treatment of obesity, but none is completely satisfactory.

SUMMARY OF THE INVENTION

It has now been found that compounds of the classes, 1,2,3,4,5,6,7,7a-octahydro-4a,7-ethanobenzofuro[3,2-e]isoquinolines (I) and 1,2,3,4,5,6,7,7a-octahydro-4a,7-ethenobenzofuro[3,2-e]isoquinolines (II), exhibit analgesic, narcotic antagonist, mixed analgesic/narcotic antagonist, and/or anorexigenic properties.

More particularly, the invention resides in the class of bridged octahydrobenzofuro[3,2-e]isoquinoline compounds which have the following formula:

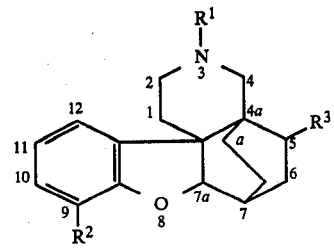

I: 3-$R^1$-9-$R^2$-5-$R^3$-1,2,3,4,5,6,7,7a-octahydro-4a,7-ethanobenzofuro[3,2-e]isoquinoline II: 3-$R^1$-9-$R^2$-5-$R^3$-1,2,3,4,5,6,7,7a-octahydro-4a,7-ethenobenzofuro[3,2-e]isoquinoline, wherein:
R¹ is selected from the group consisting of —H, $C_{1-10}$ alkyl, —CH₂R⁶,

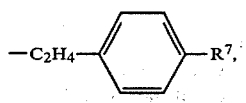

and —(CH₂)$_n$CN in which n=1-3 inclusive;
R₂ is selected from the group consisting of —H, —OH, $C_{1-2}$ alkoxy and $C_{2-12}$ acyloxy of an alkanoic acid;
R³ is selected from the group consisting of —H, $C_{1-8}$ alkyl, and —C(OH)(R⁴)R⁵;
a is a single bond (I) or double bond (II);
R⁴ is selected from the group consisting of —H, and $C_{1-8}$ alkyl;
R⁵ is selected from the group consisting of —H, $C_{1-8}$ alkyl, $C_{1-8}$ alkenyl, $C_{1-8}$ cycloalkyl, and —(CH₂)$_m$C₆H₅ in which m=0-4 inclusive;
R⁶ is selected from the group consisting of

—C≡CH, $C_{3-6}$ cycloalkyl, phenyl, 2-thienyl, 2-furyl and 2-tetrahydrofuryl of which the latter two may be substituted with a methyl group;
R⁷ is selected from the group consisting of —H, $C_{1-3}$ alkyl, —OCH₃, —Cl, —Br and —F; and each of
R⁸ and R⁹ is independently selected from the group consisting of —H, —CH₃ and —Cl.

It is intended that the above formula include within its description the racemates and the dextro- and laevorotatory antipodes thereof, pharmaceutically suitable acid addition salts thereof, and N-oxides thereof.

The invention also resides in compositions comprising the above-described compounds and a pharmaceutical carrier and in methods for the treatment of pain and/or alleviating the effect of a narcotic drug and/or exerting an anorexigenic effect, in a mammal, said methods comprising administering internally to the mammal an effective analgesic or antagonist or anorexigenic amount of the above-described compounds of the invention. Processes for preparing the compounds of this invention and intermediates used therein are also part of this invention.

DETAILED DESCRIPTION OF THE INVENTION

The compounds of the invention, I and II, can be prepared by procedures such as those illustrated by the examples below. The compounds can be prepared from 2,3-dihydro-1H-benzofuro[3,2-e]isoquinoline-4(7aH)-ones (III).

The following equations illustrate reactions useful in the preparation of compounds of the invention:

Variation of R³

R³=H, $C_{1-8}$ Alkyl
The compounds of the invention I in which R³ is H or $C_{1-8}$ alkyl can be synthesized by the following general sequence of reactions:

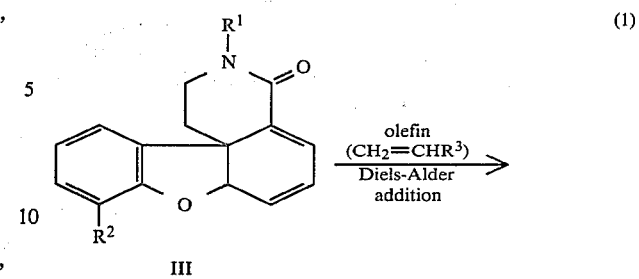

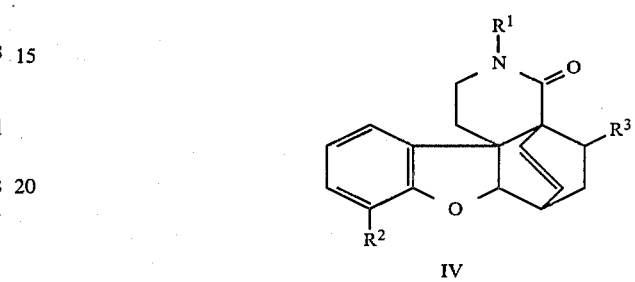

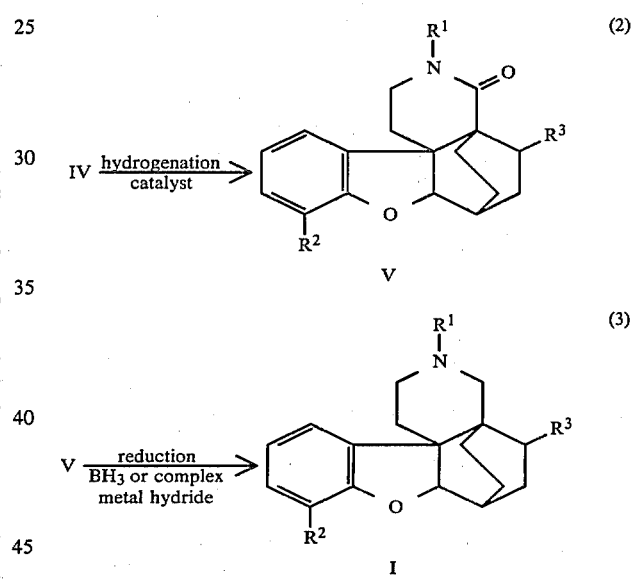

Reactions 1-3 are exemplified in Examples 1-6 for the case of R³=H. Compounds II, i.e., wherein a is a double bond, in which R³=H or $C_{1-8}$ alkyl can be prepared by the following reaction:

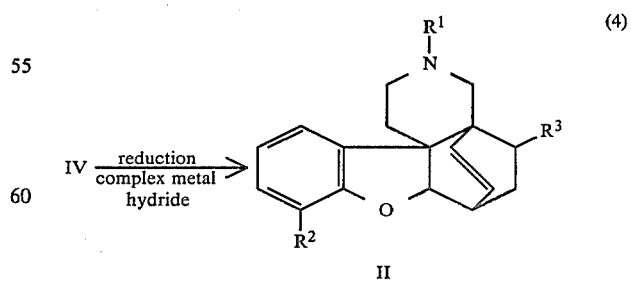

R³=CH₂OH (R⁴=R⁵=H)
The compounds of the invention I in which R³ is CH₂OH (i.e., R⁴=R⁵=H) can be prepared by carrying out reactions 1 and 2 in which R³ is replaced by $CO_2R^{10}$ and $R^{10}$ is lower alkyl or benzyl, followed by the reaction:

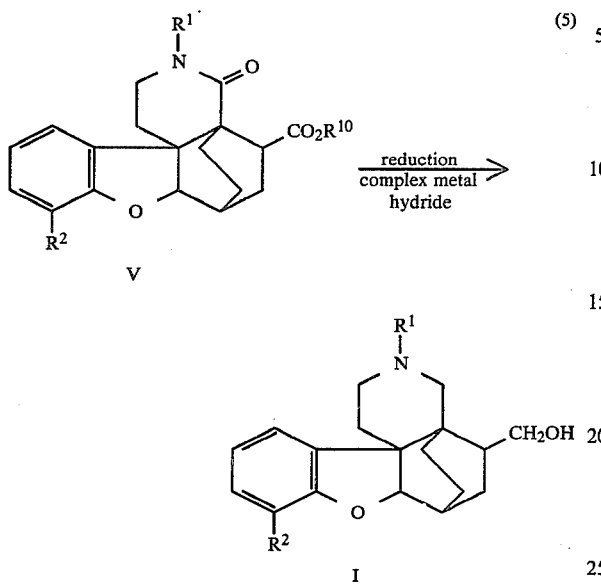

This process, i.e., carrying out reactions 1, 2 and 5 as described, is illustrated in Example 9. Compounds II in which $R^3=CH_2OH$ can be prepared by reaction 4 wherein in Compound IV, $R^3$ is replaced by $CO_2R^{10}$.

$R^3=CH(OH)R^5$ ($R^4=H$, $R^5 \neq H$)

The compounds of the invention I in which $R^4$ is H and $R^5$ is not H can be prepared by carrying out reaction 1 wherein $R^3$ is replaced by $COR^5$, followed by the reaction:

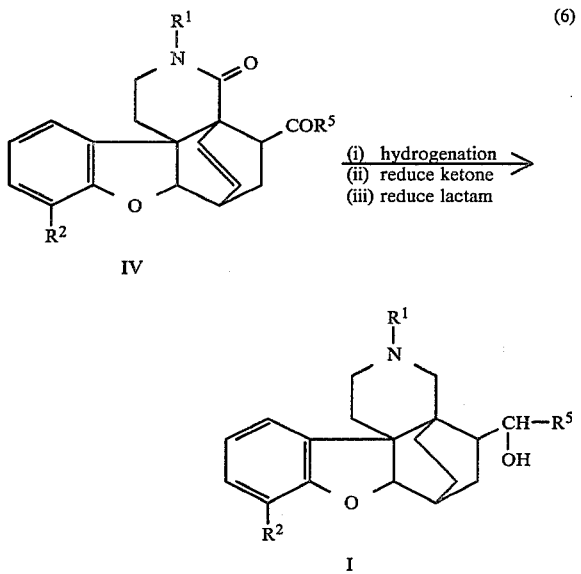

This process, i.e., carrying out reactions 1 and 6, is exemplified for $R^5$=methyl ("Me") in Examples 7 and 10. Compounds II in which $R^3=CH(OH)R^5$ can be prepared by the reaction of Equation 4, as illustrated in Example 8, wherein $R^3$ is replaced by $COR^5$.

$R^3=C(R^4)(R^5)OH$, $R^4 \neq H$, $R^5 \neq H$

The compounds of the invention II in which neither $R^4$ nor $R^5$ is hydrogen can be prepared by carrying out reaction 1 in which $R^3$ is replaced by $COR^5$, followed by the reaction:

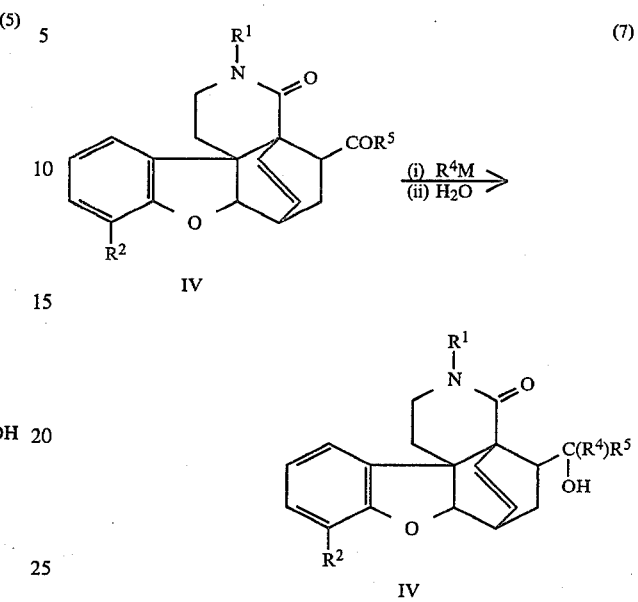

$R^4M$ is an organometallic reagent, e.g., M is MgCl, MgBr (Grignard reagents) or Li (organolithium reagents).

Compounds IV in which $R^3=C(OH)(R^4)R^5$ from reaction 7 can then be reduced as in reaction 4 to provide Compounds II in which $R^3=C(OH)(R^4)R^5$. Compounds I in which $R^3=C(OH)(R^4)R^5$ can be prepared by catalytic hydrogenation of II or by carrying out reactions 1 and 2, in which $R^3$ is replaced by $COR^5$, followed by reactions 7 and 3.

The process of carrying out reactions 1, 2, 7 and 3 to prepare said Compounds I is illustrated in Example 11 for the case of $R^4$=t-butyl and $R^5$=Me.

The sequence in which $R^4$ and $R^5$ are introduced may be changed, i.e., the Diels-Alder addition of reaction 1 may be carried out with $R^3$ replaced by $COR^4$, followed by reaction with $R^5M$ in reaction 7.

To avoid any undesired side reaction of $R^4M$ with the lactam function of IV in which $R^3$ is replaced by $COR^5$, during reaction 7, the lactam may optionally be reduced first, as in reaction 4; such reduction will also cause reduction of the carbonyl group ($COR^5$) to an alcohol function ($CH(OH)R^5$); however, the secondary alcohol can easily be reoxidized to a ketone, II in which $R^3$ is replaced by $COR^5$, with oxidizing agents, including, e.g., chromic anhydride, pyridinium chlorochromate, other Cr(VI)-based oxidants, and other oxidizing agents. The compounds II and I ($R^3=C(OH)(R^4)R^5$) are prepared from II in which $R^3$ is replaced by $COR^5$ by organometallic addition as in reaction 7 to yield II, followed by catalytic hydrogenation to yield I.

Variation of $R^1$

By using $R^1NH_2$ as the amine in the synthesis of III, compounds III can be obtained in which $R^1=C_{1-10}$ alkyl, $-CH_2R^6$ ($R^6=C_{3-6}$ cycloalkyl, phenyl, tetrahydrofuryl, and methyltetrahydrofuryl), and

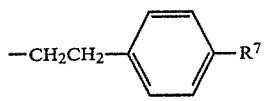

($R^7$=—H, $C_{1-3}$ alkyl, —OCH$_3$, —Cl, —Br, or —F). These derivatives of III may be transformed into the compounds of the invention, I and II, by the reactions described above. Alternatively, these groups can be introduced into I or II in which $R^1$=H (which may be prepared as described below) by acylation followed by reduction or by direct alkylation.

For example, compounds of the invention II in which $R^1$=H may be treated with tetrahydrofuroyl chloride in the presence of a base such as aqueous sodium hydroxide solution, which, when followed by reduction with lithium aluminum hydride gives II ($R^1$=

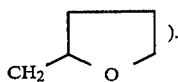

Likewise, using cyclopropanecarbonyl chloride, 9-methoxy-1,2,3,4,5,6,7,7a-octahydro-4a,7-ethenobenzofuro[3,2-e]isoquinoline (II; $R^1$=H, $R^2$=OMe, $R^3$=H) is transformed into 3-cyclopropylmethyl-9-methoxy-1,2,3,4,5,6,7,7a-octahydro-4a,7-ethenobenzofuro[3,2-e]isoquinoline (II; $R^1$=cyclopropylmethyl, $R^2$=OMe, $R^3$=H).

In a typical alkylation procedure, 9-methoxy-1,2,3,4,5,6,7,7a-octahydro-4a,7-ethanobenzofuro[3,2-e]isoquinoline (I; $R^1$=H, $R^2$=OMe, $R^3$=H) is treated with allyl bromide in the presence of a base such as potassium carbonate in a solvent such as dimethylformamide to give 3-allyl-9-methoxy-1,2,3,4,5,6,7,7a-octahydro-4a,7-ethanobenzofuro[3,2e]isoquinoline (I; $R^1$=CH$_2$CH=CH$_2$, $R^2$=OMe, $R^3$=H).

Preparation of I ($R^1$=H)

If benzylamine is used in the synthesis of III, there is obtained 3-benzyl-9-methoxy-2,3-dihydro-1H-benzofuro[3,2-e]isoquinoline (III; $R^1$=CH$_2$C$_6$H$_5$, $R^2$=OMe, $R^3$=H), which can be converted into 3-benzyl-9-methoxy-1,2,3,4,5,6,7,7a-octahydro-4a,7-ethanobenzofuro[3,2-e]isoquinoline (I; $R^1$=CH$_2$C$_6$H$_5$, $R^2$=OMe, $R^3$=H), e.g., as illustrated in Example 1. By catalytic hydrogenolysis such as hydrogenation over a palladium catalyst, I ($R^1$=CH$_2$C$_6$H$_5$, $R^2$=OMe, $R^3$=H) may be transformed into 9-methoxy-1,2,3,4,5,6,7,7a-octahydro-4a,7-ethanobenzofuro[3,2-e]isoquinoline (I; $R^1$=H, $R^2$=OMe, $R^3$=H).

Preparation of II ($R^1$=H)

When 3-benzyl-9-methoxy-2,3-dihydro-1H-benzofuro[3,2-e]isoquinoline (III; $R^1$=CH$_2$C$_6$H$_5$, $R^2$=OMe) is subjected to the first process step of Example 1 and the first process step of Example 8, there is obtained 3-benzyl-9-methoxy-1,2,3,4,5,6,7,7a-octahydro-4a,7-ethenobenzofuro[3,2-e]isoquinoline, (II; $R^1$=CH$_2$Ph, $R^2$=MeO, $R^3$=H). By standard methods, such as the von Braun cyanogen bromide reaction followed by hydrolysis, or treatment with 2,2,2-trichloroethyl chloroformate followed by zinc dust reduction, there is obtained 9-methoxy-1,2,3,4,5,6,7,7a-octahydro-4a,7-ethenobenzofuro[3,2-e]isoquinoline (II; $R^1$=H, $R^2$=OMe, $R^3$=H).

Variation of $R^2$

The methoxy derivatives I and II ($R^2$=OMe), discussed in the Examples may be considered representative of the compounds in which $R^2$ is H or alkoxy. These latter derivatives are accessible by starting with the appropriately 9-unsubstituted or 9-alkoxy-substituted 2,3-dihydro-1H-benzofuro[3,2-e]isoquinolin-4(7aH)-ones (III) and using the processes detailed above. Alternatively, the phenols I or II ($R^2$=OH) may be alkylated, for instance with ethyl iodide and sodium hydride to provide I or II ($R^2$=OC$_2$H$_5$). C$_{2-12}$ acyloxy is introduced by acylating the phenols I or II ($R^2$=OH) by standard methods.

The phenols I or II ($R^2$=OH) are prepared by demethylation of the methoxy compounds with a potassium thiolate as described in Examples 2,4,6,7,8,9,10 and 11. Other methods known to those skilled in the art, involving reagents such as pyridine hydrochloride or lithium thiomethoxide, may be used to effect dealkylation of alkoxy compounds to the corresponding phenols.

Process Variables

The Diels-Alder Additions [III→IV, e.g., reaction 1] can be carried out in the absence of a solvent or using invert solvents such as aromatic hydrocarbons, chlorinated aromatic hydrocarbons and aliphatic or aromatic ethers. The reaction may be carried out at temperatures of about 50 to about 250° C. for several minutes to several weeks. To avoid yield loss due to polymerization of III, the reaction may be carried out in an evacuated steel or glass vessel after the reactants and/or reactant solution has been thoroughly degassed. Undesirable polymerization of III can also be minimized by the presence of a free radical polymerization inhibitor, such as phenothiazine.

Catalytic Reductions [IV→V, e.g., reaction 2, 6-Step i; II→I] are carried out by conventional catalytic hydrogenation in the liquid phase at about 20° to about 100° C. Conventional hydrogenation catalysts such as Raney nickel, platinum and palladium, any of which can be supported on suitable carriers, can be used. The reaction is carried out with an excess of hydrogen and at comparatively mild conditions of temperature and pressure in order to reduce the double bond but not the benzene ring.

Reductions of Lactam to Amine [V→I, e.g., reactions 3, 5, 6-Step iii; IV→II, e.g., reaction 4] involve the use of a complex metal hydride, such as LiAlH$_4$ or BH$_3$.(CH$_3$)$_2$S or BH$_3$.tetrahydrofuran. Borane is preferred in the complex because it is both inexpensive and easy to handle safely. When reducing compounds containing multiple carbon-carbon bonds, it is preferable to use LiAlH$_4$ in order to avoid borane addition to the carbon-carbon bonds. To obtain a satisfactorily rapid reaction rate, the reaction should be carried out in the liquid phase at a temperature of at least about 50° C. A preferred method of carrying out the reaction is solvent reflux, whereby the reaction is effected at essentially the boiling point of the solvent used, such as tetrahydrofuran. When a metal hydride complex, such as BH$_3$.tetrahydrofuran or BH$_3$.dimethyl sulfide is used, the complex is decomposed upon completion of the reaction by heating the reaction system with acid, preferably an organic acid such as acetic acid.

Ketone Reductions [V ($R^3$ is replaced by COR$^5$)→V ($R^3$=CH(OH)R$^5$), Equation 6-Step ii] can be carried out using a mild hydride reducing agent such as sodium borohydride in an alcohol solvent. A stronger reducing agent such as LiAlH$_4$ also effects the ketone reduction.

Conversion of Ketones to Tertiary Alcohols [IV or V (R$^3$ is replaced by COR$^5$)→IV or V (R$^3$=C(OH)(R$^4$)R$^5$), e.g., reaction 7; II (R$^3$ is replaced by COR$^5$)→II (R$^3$=C(OH)(R$^4$)R$^5$] can be effected by the use of organometallic reagents such as R$^4$M, where M may be, e.g., MgI, MgBr, or MgCl (Grignard reagents), or Li (organolithium reagents).

Oxidation of Secondary Alcohols to Ketones [II (R$^3$=CH(OH)R$^5$)→II (R$^3$ is replaced by COR$^5$)], is carried out using chromic anhydride, pyridinium chlorochromate, other Cr(VI)-based oxidants, or other oxidizing agents known to those skilled in the art.

The compounds of the invention can be readily converted to the corresponding acid addition salts which have increased water solubility. Such salts include those made with physiologically acceptable acids which are known in the art, e.g., hydrochloride, sulfate, nitrate, phosphate, tartrate and maleate salts.

EXAMPLES

The compounds of the invention, their use and the processes for making them will be better understood by reference to the following illustrative examples, in which all indications of percentage are by weight unless otherwise indicated and temperatures are in degrees Celsius.

In these molecules d and l optical isomers occur as racemic mixtures which can be resolved by known methods (e.g., Eliel, *Stereochemistry of Carbon Compounds*, McGraw-Hill, 1962, page 21). The optical isomers corresponding to the absolute configuration of morphine are preferred.

Table 1 summarizes the compounds prepared in Examples 1 to 11, the last four column headings being the symbols shown in formulas I and II for the compounds of the invention. In Examples 4 and 6, the compounds were converted to the hydrochloride salts thereof. OMe means methoxy; n-Pr means n-propyl; and t-Bu means t-butyl.

TABLE 1

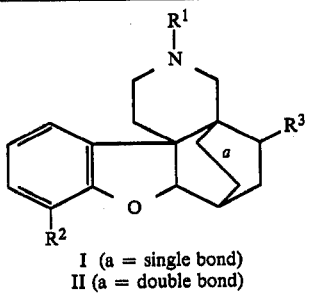

I (a = single bond)
II (a = double bond)

| Example | R$^1$ | R$^2$ | R$^3$ | a |
|---|---|---|---|---|
| 1 | Me | OMe | H | single bond |
| 2 | Me | OH | H | " |
| 3 | n-Pr | OMe | H | " |
| 4 | n-Pr | OH | H | " |
| 5 | ▷—CH$_2$ | OMe | H | " |
| 6 | ▷—CH$_2$ | OH | H | " |
| 7 | ▷—CH$_2$ | OH | CH(OH)Me | " |

TABLE 1-continued

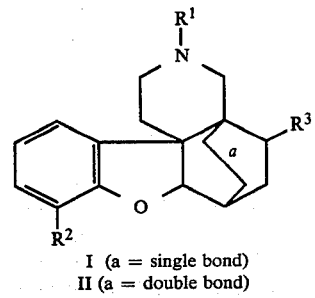

I (a = single bond)
II (a = double bond)

| Example | R$^1$ | R$^2$ | R$^3$ | a |
|---|---|---|---|---|
| 8 | ▷—CH$_2$ | OH | CH(OH)Me | double bond |
| 9 | ▷—CH$_2$ | OH | CH$_2$OH | single bond |
| 10* | ▷—CH$_2$ | OH | CH(OH)Me | " |
| 11 | ▷—CH$_2$ | OH | C(OH)(t-Bu)Me | " |

*Two isomers of the compound of Example 7

EXAMPLE 1

9-Methoxy-3-methyl-1,2,3,4,5,6,7,7a-octahydro-4a,7-ethanobenzofuro[3,2-e]isoquinoline A mixture of 3 g of 9-methoxy-3-methyl-2,3-dihydro-1H-benzofuro[3,2-e]isoquinolin-4(7aH)-one (III); R$^1$=Me, R$^2$=OMe; prepared as described in U.S. Pat. Nos. 4,260,761 and 4,243,668, 0.1 g of phenothiazine, and 30 mL of toluene, contained in an autoclave, was heated under 1000 atm (130,000 kPa) ethylene pressure to 180° for 8 hours. Removal of the solvent gave 3.2 g of crude 9-methoxy-3-methyl-1,2,5,6,7,7a-hexahydro-4a,7-ethenobenzofuro[3,2-e]isoquinolin-4(3H)-one (IV; R$^1$=Me, R$^2$=OMe, R$^3$=H) which was purified by sublimation [180° bath, 1 μm (0.1 Pa)].

NMR spectrum (220 MHz, in CDCl$_3$): τ3.4 (m, 2); 3.7 (d, J=8 Hz, 1); 3.8 (t, J=5 Hz, 1); 4.0 (d/d, J=6/8 Hz, 1); 5.5 (d, J=3 Hz, 1); 6.1 (s, 3); 6.3 (m, 1); 6.5 (d/d, J=7/13 Hz, 1); 6.8 (s, 3); and 7.7-8.8 (m, 7).

A solution of 0.83 g of this product in tetrahydrofuran was stirred with 0.22 g of 10% palladium on charcoal under hydrogen for 45 minutes.

The 9-methoxy-3-methyl-1,2,5,6,7,7a-hexahydro-4a,7-ethanobenzofuro[3,2-e]isoquinolin-4(3H)-one (V; R$^1$=Me, R$^2$=OMe, R$^3$=H) so obtained was heated under reflux with 0.7 mL of borane-methyl sulfide in tetrahydrofuran overnight. Conc. hydrochloric acid was added, the tetrahydrofuran was removed, and the residue was heated under reflux with 7 mL of acetic acid and 3 mL of conc. hydrochloric acid for two hours. The solvents were removed, water and toluene were added, and the aqueous layer was made basic and extracted with methylene chloride. Removal of the solvent and short-path distillation of the residue [150° bath, 0.5 μm (0.07 Pa)] gave 0.52 g of 9-methoxy-3-methyl-1,2,3,4,5,6,7,7a-octahydro-4a,7-ethanobenzofuro[3,2-e]isoquinoline as a viscous oil that slowly solidified. NMR spectrum (220 MHz in CDCl$_3$): τ3.1 (d/d, J=6.5/2.5 Hz, 1); 3.5 (m, 2); 5.7 (narrow m, 1); 6.2 (s, 3); 8.0 (s, 3); and 7.5-9.3 (m, 15).

EXAMPLE 2

3-Methyl-1,2,3,4,5,6,7,7a-octahydro-4a,7-ethanobenzofuro[3,2-e]isoquinolin-9-ol A mixture of 2.69 g of crude 9-methoxy-3-methyl-1,2,3,4,5,6,7,7a-octahydro-4a,7-ethanobenzofuro[3,2-e]isoquinoline, (prepared as described above in Example 1), 2.7 g of potassium t-butoxide, 30 mL of dry dimethylformamide and 3 mL of n-propyl mercaptan was heated to 135° for 6 hours. Acetic acid (3 mL) was added to the cooled mixture, the solvents were removed, and the residue was partitioned between ether and dilute hydrochloric acid. The aqueous acidic phase was made basic with 10% aqueous sodium carbonate solution and extracted with methylene chloride. Removal of the solvent from the dried solution and sublimation of the residue [185° bath, 5 μm (0.7 Pa)] gave 2.12 g of product which on crystallization from 90% aqueous ethanol gave 1.27 g of 3-methyl-1,2,3,4,5,6,7,7a-octahydro-4a,7-ethanobenzofuro[3,2-e]isoquinolin-9-ol, m.p. 174°–176°.

Anal. Calcd. for $C_{18}H_{23}NO_2$: C, 75.75; H, 8.12; N, 4.91. Found: C, 76.06; H, 8.03; N, 4.77.

EXAMPLE 3

9-Methoxy-3-propyl-1,2,3,4,5,6,7,7a-octahydro-4a,7-ethanobenzofuro[3,2-e]isoquinoline Following the procedure of Example 1, but using 3.1 g of 9-methoxy-3-propyl-2,3-dihydro-1H-benzofuro[3,2-e]isoquinolin-4(7aH)-one (III; $R^1$=n-Pr, $R^2$=OMe) as the starting material, there was obtained 2.1 g of 9-methoxy-3-propyl-1,2,3,4,5,6,7,7a-octahydro-4a,7-ethanobenzofuro[3,2-e]isoquinoline.

NMR spectrum (220 MHz in CDCl$_3$): τ2.8 (d/d, J=6.5/2.5 Hz, 1); 3.2 (m, 2); 5.5 (narrow m, 1); 6.0 (s, 3); 7.1–9.0 (m, 19); and 9.0 (t, J=7 Hz, 3).

EXAMPLE 4

3-Propyl-1,2,3,4,5,6,7,7a-octahydro-4a,7-ethanobenzofuro[3,2-e]isoquinolin-9-ol Following the procedure of Example 2, but using 1.97 g of 9-methoxy-3-propyl-1,2,3,4,5,6,7,7a-octahydro-4a,7-ethanobenzofuro[3,2-e]isoquinoline (Example 3) as the starting material, there was obtained 2.18 g of 3-propyl-1,2,3,4,5,6,7,7a-octahydro-4a,7-ethanobenzofuro[3,2-e]isoquinolin-9-ol.

NMR spectrum (220 MHz in CDCl$_3$): 3.0 (d/d, J=7/2 Hz, 1); 3.3 (d/d, J=7/2 Hz, 1); 3.4 (t, J=7 Hz, 1); 4.3 (broad s, 1); 5.7 (narrow m, 1); 7.2–9.0 (m, 19); and 9.1 (t, J=7 Hz, 3).

Mass spectrum: m/z calcd., 313.2040; found: 313.2035.

The 3-propyl-1,2,3,4,5,6,7,7a-octahydro-4a,7-ethanobenzofuro[3,2-e]isoquinolin-9-ol was converted to its hydrochloride salt and crystallized from ethanol to provide 1.52 g of 3-propyl-1,2,3,4,5,6,7,7a-octahydro-4a,7-ethanobenzofuro[3,2-e]isoquinolin-9-ol hydrochloride, m.p. 200°–202°.

EXAMPLE 5

3-Cyclopropylmethyl-9-methoxy-1,2,3,4,5,6,7,7a-octahydro-4a,7-ethanobenzofuro[3,2-e]isoquinoline Following the procedure of Example 1, but using 3-cyclopropylmethyl-9-methoxy-2,3-dihydro-1H-benzo-furo[3,2-e]isoquinolin-4(7aH)-one (III;

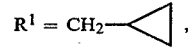

$R^2$=OMe) as starting material, there was obtained 3-cyclopropylmethyl-9-methoxy-1,2,3,4,5,6,7,7a-octahydro-4a,7-ethanobenzofuro[3,2-e]isoquinoline.

NMR spectrum (220 MHz in CDCl$_3$): τ2.5 (d/d, J=7/2 Hz, 1); 3.0 (m, 2); 5.3 (narrow m, 1); 5.8 (s, 3); 6.8–8.2 (m, 18); 9.2 (m, 2); and 9.5 (m, 2).

This material was converted to its hydrochloride salt with methanolic hydrogen chloride; crystallization from 90% aqueous ethanol provided 3-cyclopropylmethyl-9-methoxy-1,2,3,4,5,6,7,7a-octahydro-4a,7-ethanobenzofuro[3,2-e]isoquinoline hydrochloride, m.p. >260°.

EXAMPLE 6

3-Cyclopropylmethyl-1,2,3,4,5,6,7,7a-octahydro-4a,7-ethanobenzofuro[3,2-e]isoquinolin-9-ol Following the procedure of Example 2, but using 3-cyclopropylmethyl-9-methoxy-1,2,3,4,5,6,7,7a-octahydro-4a,7-ethanobenzofuro[3,2-e]isoquinoline (Example 5) as the starting material, there was obtained 3-cyclopropylmethyl-1,2,3,4,5,6,7,7a-octahydro-4a,7-ethanobenzofuro[3,2-e]isoquinolin-9-ol as the hydrochloride, m.p. >260°.

NMR spectrum of the free base (220 MHz in CDCl$_3$): τ3.0 (d/d, J=7/2 Hz, 1); 3.3 (d/d, J=7/2 Hz, 1); 3.4 (t, J=7 Hz, 1); 5.7 (narrow m, 1); 7.0–9.2 (m, 18); 9.5 (m, 2); and 9.9 (m, 2).

EXAMPLE 7

3-Cyclopropylmethyl-5-(1-hydroxyethyl)-1,2,3,4,5,6,7,7a-octahydro-4a,7-ethanobenzofuro[3,2-e]isoquinolin-9-ol A mixture of 3.02 g of 3-cyclopropylmethyl-9-methoxy-2,3-dihydro-1H-benzofuro[3,2-e]isoquinolin-4-(7aH)-one (III,

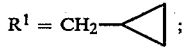

$R^2$=OMe), 15 mL of toluene, 0.07 g of phenothiazine, and 12 mL of methyl vinyl ketone, contained in an evacuated, sealed Carius tube, was heated to 120° for 4 hours. Removal of the solvent and crystallization of the residue from ethyl acetate gave 2.20 g of 5-acetyl-3-cyclopropylmethyl-9-methoxy-1,2,5,6,7,7a-hexahydro-4a,7-ethanobenzofuro[3,2-e]isoquinolin-4(3H)-one (IV;

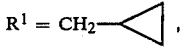

$R^2$=OMe, $R^3$=COMe), m.p. 179°–192°.

NMR spectrum (220 MHz in CDCl$_3$): τ3.2 (m, 2); 3.3 (m, 1); 3.7 (m, 2); 5.4 (d, J=2.5 Hz, 1); 6.0–6.8 (m+s, 9); 7.5 (m, 1); 7.7–7.9 (m+s, 4); 8.2 (m, 2); 8.7 (m, 1); 9.3 (m, 2); and 9.6 (m, 2).

Anal. Calcd. for $C_{24}H_{27}NO_4$: C, 73.26; H, 6.92; N, 3.56. Found: C, 73.26; H, 6.90; N, 3.59.

The crystal structure was determined by standard X-ray diffraction techniques. Crystals of the compound are orthorhombic, space group $P2_12_12_1$, with a=6.665(2), b=16.225(4), and c=18.471(4) Å at −100°. The cyclopropyl moiety was found to be disordered; a suitable model to account for the disorder was refined and led to R=0.078 using intensity data for 2028 reflections. The structure is as follows:

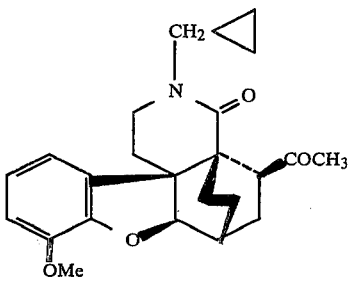

A solution of 1.26 g of 5-acetyl-3-cyclopropylmethyl-9-methoxy-1,2,5,6,7,7a-hexahydro-4a,7-ethenobenzofuro[3,2-e]isoquinolin-4 (3H)-one in tetrahydrofuran was stirred with 0.22 g of 10% palladium on charcoal under hydrogen for 20 hours. Removal of the solvent from the filtered solution gave 1.34 g of crude 5-acetyl-3-cyclopropylmethyl-9-methoxy-1,2,5,6,7,7a-hexahydro-4a,7-ethanobenzofuro[3,2-e]isoquinolin-4(3H)-one (V;

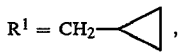

$R^2$=OMe, $R^3$=COMe). This product was stirred with 5 mL of ethanol and 0.24 g of sodium borohydride, first in an ice bath, then at room temperature, for 20 hours. Excess borohydride was decomposed with 10% hydrochloric acid, the mixture was made basic and extracted with methylene chloride to give 1.31 g of 3-cyclopropylmethyl-5-(1-hydroxyethyl)-9-methoxy-1,2,5,6,7,7a-hexahydro-4a,7-ethanobenzofuro[3,2-e]isoquinolin-4(3H)-one (V;

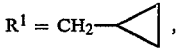

$R^2$=OMe, $R^3$=CH(OH)Me) as a mixture of threo and erythro isomers.

NMR spectrum (220 MHz in CDCl₃): 3.2–3.4 (m, 3); 5.2 (narrow m, 0.3); 5.3 (narrow m, 0.7); 5.6–5.9 (m+s, 5); 6.0–8.9 (m, including two 6 Hz doublets, 18); 9.4 (m, 2); and 9.6 (m, 2).

This product was reduced with borane-methyl sulfide as described in Example 1 to give 1.34 g of crude 3-cyclopropylmethyl-5-(1-hydroxyethyl)-9-methoxy-1,2,3,4,5,6,7,7a-octahydro-4a,7-ethanobenzofuro-[3,2-3]isoquinoline (I;

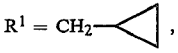

$R^2$=OMe, $R^3$=CH(OH)Me) as a mixture of threo and erythro isomers.

This product was demethylated as described in Example 2 to give 3-cycloporpylmethyl-5-(1-hydroxyethyl)-1,2,3,4,5,6,7,7a-octahydro-4a,7-ethanobenzofuro[3,2-e]isoquinolin-9-ol as a mixture of threo and erythro isomers, m.p. 255°–258° after crystallization from dimethylformamide.

Anal. Calcd. for $C_{23}H_{31}NO_3$: C, 74.76; H, 8.46; N, 3.79. Found: C, 74.54; H, 8.41; N, 3.86.

Mass Spectrum: m/z calcd., 369.2270; found, 369.2302.

EXAMPLE 8

3-Cyclopropylmethyl-5-(1-hydroxyethyl)-1,2,3,4,5,6,7,7a-octahydro-4a,7-ethenobenzofuro[3,2-e]isoquinolin-9-ol A mixture of 0.51 g of 5-acetyl-9-methoxy-3-cyclopropylmethyl-1,2,5,6,7,7a-hexahydro-4a,7-ethenobenzofuro[3,2-e]isoquinolin-4(3H)-one (Example 7), 0.8 g of lithium aluminum hydride and tetrahydrofuran was heated under reflux for 24 hours. Conventional workup gave 0.48 g of crude 9-methoxy-3-cyclopropylmethyl-5-(1-hydroxyethyl)-1,2,3,4,5,6,7,7a-octahydro-4a,7-ethenobenzofuro[3,2-e]isoquinoline as a mixture of threo and erythro isomers. Demethylation as described in Example 2 and cyrstallization from a mixture of ethanol and 2-propanol gave 0.20 g of 3-cyclopropylmethyl-5-(1-hydroxyethyl)-1,2,3,4,5,6,7,7a-octahydro-4a,7-ethenobenzofuro[3,2-e]isoquinolin-9-ol, as a mixture of threo and erythro isomers, m.p. 170°–190°.

Mass spectrum: m/z calcd., 367.2146; found, 367.2147.

EXAMPLE 9

3-Cyclopropylmethyl-5-hydroxymethyl-1,2,3,4,5,6,7,7a-octahydro-4a,7-ethanobenzofuro[3,2-e]isoquinolin-9ol A mixture of 1.50 g of 3-cyclopropylmethyl-9-methoxy-2,3-dihydro-1H-benzofuro[3,2-e]isoquinolin-4-(7aH)-one (III;

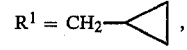

$R^2$=OMe), 10 mL of methyl acrylate and 0.01 g of phenothiazine, contained in an evacuated and sealed Carius tube, was heated to 130° for 6 hours. Removal of the excess methyl acrylate gave 2.17 g of 3:1 mixture of two isomers of 3-cyclopropylmethyl-9-methoxy-5-methoxycarbonyl-1,2,5,6,7,7a-hexahydro-4a,7-ethenobenzofuro[3,2-e]isoquinolin-4(3H)-one (IV;

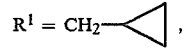

$R^2$=OMe, $R^3$=CO₂CH₃). 220 MHz NMR spectroscopy showed that the major isomer had the same stereochemistry as the corresponding methyl vinyl ketone adduct (Example 7). The mixture was subjected to catalytic hydrogenation (30 mL tetrahydrofuran, 1.04 g of 10% Pd/C, room temperature, overnight) and the product so obtained was hydrolyzed by heating under reflux with aqueous methanolic sodium hydroxide followed by acidification to give 1.52 g of 5-carboxy-3-cyclopropylmethyl-9-methoxy-1,2,5,6,7,7a-hexahydro-4a,7-ethanobenzofuro[3,2-e]isoquinolin-4(3H)-one (V;

$R^1 = CH_2-$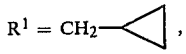, $R^2$=OMe, $R^3$=CO$_2$H) as a mixture of two isomers. Reduction with borane methyl sulfide and demethylation as described in Examples 1 and 2 gave 1.72 g of crude product which on crystallization from dimethylformamide gave 0.62 g of a single isomer of 3-cyclopropylmethyl-5-hydroxymethyl-1,2,3,4,5,6,7,7a-octahydro-4a,7-ethanobenzofuro[3,2-e]isoquinolin-9-ol, m.p. 187°–190°.

Anal. Calcd. for $C_{22}H_{29}NO_3$; C, 74.33; H, 8.22; N, 3.94. Found: C, 74.03; H, 8.16; N, 4.10.

EXAMPLE 10

3-Cyclopropylmethyl-5- or -6-(1-hydroxyethyl)-1,2,3,4,5,6,7,7a-octahydro-4a,7-ethanobenzofuro[3,2-e]isoquinolin-9-ol (two isomers of the product of Example 7)

High-pressure liquid chromatography of the mother liquor from 5-acetyl-3-cyclopropylmethyl-9-methoxy-1,2,5,6,7,7a-hexahydro-4a,7-ethenobenzofuro[3,2-e]isoquinolin-4(3H)-one (Example 7) gave two additional isomeric methyl vinyl ketone adducts in 10% and 1% yield, respectively. The 10% isomer had the following NMR spectrum (220 MHz in CDCl$_3$): $\tau$3.3–3.4 (m, 3); 3.6 (d, J=8 Hz, split further, 1); 4.1 (d/d, J=8/6 Hz, 1), 5.4 (d, J=3 Hz, 1); 6.0–6.2 (m+s, 4); 6.3.–6.5 (m, 3); 6.7 (d/d, J=13/7 Hz, 1); 7.3 (m, 1); 7.6–7.9 (m+s, 6), 8.1 (d/d, J=13/6 Hz, 1); 8.8 (m, 1); 9.4 (m, 2) and 9.6 (m, 2). The 1% isomer had the following NMR spectrum (220 MHz in CDCl$_3$): $\tau$3.4 (m, 3); 3.5 (d/d, J=8/1.5 Hz, 1); 4.0 (d/d, J=8/6 Hz, 1); 5.4. (d, J=3 Hz, 1); 6.2 (s, 3); 6.3 (m, 2); 6.6 (d/d, J=13/8 Hz, 1); 6.8 (m, 2); 7.0 (d/d, J=11/8 Hz, 1); 7.5 (m, 1); 7.8 (s, 3); 7.9 (m, 1); 8.1 (d/d, J=13/7 Hz, 1); 8.4 (m, 1); 8.8 (m, 1); 9.4 (m, 2); and 9.6 (m, 2).

Using the procedures described in Example 7, both isomers were converted to 3-cyclopropylmethyl-5- or 6-(1-hydroxyethyl)-1,2,3,4,5,6,7,7a-octahydro-4a,7-ethanobenzofuro[3,2-e]isoquinolin-9-ol. The product from the 10% isomer had m.p. 181°–184°.

NMR spectrum (220 MHz in CDCl$_3$): $\tau$3.0 (d/d, J=7.2 Hz, 1); 3.4 (d/d, J=7/2 Hz, 1); 3.5 (t, J=7 Hz, 1); 5.7 (d, J 2 Hz, 1); 6.3 (m, 1); 7.0–8.7 (m, 14); 8.8 (d, J=6 Hz, 3) 8.9 (m, 1); 9.1 (m, 2); 9.3–9.5 (m, 3); and 9.9 (m, 2).

Mass spectrum: m/z calcd. for $C_{23}H_{31}NO_3$, 369.2304; found, 369.2325.

The product from the 1% isomer had m.p. 228°–230°.

NMR spectrum (220 MHz in CDCl$_3$): $\tau$3.0 (d, J=8 Hz, split further, 1); 3.2 (d, J=8 Hz, split further, 1); 3.4 (t, J=8 Hz, 1); 5.6 (narrow m, 1); 6.2 (m, 1); 7.0–7.7 (m, 6); 7.7–9.2 (m, 12); 8.8 (d, J=6 Hz, 3); 9.4 (m, 2) and 9.8 (m, 2).

Mass spectrum: m/z calcd. for $C_{23}H_{31}NO_3$, 369.2304; found, 369.2316.

EXAMPLE 11

3-Cyclopropylmethyl-5-(2-hydroxy-3,3-dimethyl-2-butyl)-1,2,3,4,5,6,7,7a-octahydro-4a,7-ethanobenzofuro[3,2-e]isoquinolin-9-ol To a mixture of 4.19 g of the major isomer of 5-acetyl-3-cyclopropylmethyl-9-methoxy-1,2,5,6,7,7a-hexahydro-4a,7-ethanobenzofuro[3,2-e]isoquinolin-4-(3H)-one (Example 7) and 50 mL of tetrahydrofuran was added, at −20°, 15 mL of 2.1 M t-butyllithium in pentane. The mixture was stirred at −10° for 5 min and treated with dilute hydrochloric acid. Extraction with ether gave 4.45 g of product which was subjected to treatment with 10 mL of t-butyllithium in the manner described above. The product so obtained was purified by high-pressure liquid chromatography to give 2.48 g of 3-cyclopropylmethyl-5-(2-hydroxy-3,3-dimethyl-2-butyl)-9-methoxy-1,2,5,6,7,7a-hexahydro-4a,7-ethanobenzofuro[3,2-e]isoquinolin-4(3H)-one (IV;

$R^1 = CH_2-$, $R^2$=OMe, $R^3$=C(OH)(CH$_3$)C(CH$_3$)$_3$) as a single isomer. NMR spectrum (220 MHz in CDCl$_3$: $\tau$3.2–3.4 (m, 3); 5.5 (narrow m, 1); 5.6 (s, 1); 6.1 (s, 3); 6.3–6.5 (m, 2); 6.6 (AB quartet, J=13 Hz split into doublets, J=7 Hz, 2); 7.4 (m, 2); 7.6–8.3 (m, 5); 8.4–9.0 (m+2s, 16); 9.4 (m, 2); and 9.6 (m, 2). This product was reduced with borane-methyl sulfide in refluxing tetrahydrofuran (40 hours) as described in Example 7 and the resulting 3-cyclopropylmethyl-5-(2-hydroxy-3,3-dimethyl-2-butyl)-9-methoxy-1,2,3,4,5,6,7,7a-octahydro-4a,7-ethanobenzofuro[3,2-e]isoquinoline was converted to 3-cyclopropylmethyl-5-(2-hydroxy-3,3-dimethyl-2-butyl)-1,2,3,4,5,6,7,7a-octahydro-4a,7-ethanobenzofuro[3,2-e]isoquinolin-9-ol, m.p. 205°–206°, using the method of Example 2.

NMR spectrum (220 MHz in hexadeuteriodimethyl sulfoxide): $\tau$2.9 (d, J=7 Hz, split further, 1); 3.4 (d, J=7 Hz, split further, 1); 3.5 (t, J=7 Hz, 1); 5.8 (d, J=3 Hz, 1); 8.7 (s, 3); and 9.0 (s, 9); inter alia.

Mass spectrum: m/z calcd. for $C_{27}H_{39}NO_3$, 425.2930; found, 425.2947.

Analgesic and Narcotic Antagonist Testing Procedures

A standard procedure for detecting and comparing the analgesic activity of compounds in this series for which there is good correlation with human efficacy is the standard phenylquinone writhing (PQW) test modified from Siegmund, et al., *Proc. Soc. Exp. Biol. Med.*, 95, 729 (1957). A test compound suspended in 1% Methocel® methyl cellulose—1.25% Tween®80 polyoxyethylene (20) sorbitan monooleate was given orally to fasted (17–21 hours) female white mice, 5–20 animals per double blind test. Aqueous (0.01% phenyl-p-benzoquinone) phenylquinone was injected intraperitoneally at 24 minutes later using 0.20 mL per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice (ED$_{50}$) was calculated by the moving average method of Thompson, W. R., *Bact. Rev.*, 11, 115–145 (1947).

Narcotic analgesics produce in mice an erection and arching of the tail (90° or more) which is referable to spinal cord stimulation. This Straub tail reaction is not produced by other analgesics, including the narcotic antagonists. Straub tail reaction tests, modified from Shemano, I., and Wendel, H., *Tox. Appl. Pharm.*, 6 334–339 (1964), were carried out at selected dosages.

Known narcotic antagonists such as naloxone and nalorphine prevent the induction of Straub tail in mice by a highly addicting agonist such as morphine [H.

Blumberg, H. B. Dayton and P. S. Wolf, *The Pharmacologist*, 10, 189 (1968)]. This property is the basis of a mouse test for narcotic antagonists.

Female CF₁S mice (fasted 17-21 hrs.), 5 or 10 per dose, were injected orally or subcutaneously with test drug at 0.67, 2, 6, 18, 54 and 162 mg/kg or other appropriate doses in 0.20 mL 1% Methocel®-1.25% Tween®80 per mouse. Five minutes later, 30 mg/kg of morphine sulfate in 0.20 mL 1% Methocel® per mouse was given intraperitoneally. Alternatively, the challenge agent was intraperitoneal etonitazene hydrochloride, given at 0.08 mg/kg. Starting ten minutes after the morphine, the mice were observed continuously for 5 minutes for evidence of Straub tail. Prevention of a 90° Straub tail during this observation period was taken as indication of narcotic antagonist ability. The effective dose at which Straub tail was prevented in 50% of the mice (ED$_{50}$) was calculated.

The analgesia and antagonist data is summarized in Table 2 below.

TABLE 2

| Example | Effect ED$_{50}$ | |
|---|---|---|
| | Oral Anti-PQW | Subcutaneous Anti-Straub Tail |
| 1 | 20.5 | >18. |
| 2 | 12. | 0.05 |
| 3 | >135. | 0.19 |
| 4$^a$ | 99. | 0.009 |
| 5 | — | — |
| 6$^a$ | 4.4 | 0.005 |
| 7 | 0.78 | 0.08 |
| 8 | 0.51 | 0.024 |
| 9 | 0.28 | 0.045$^c$ |
| 10 (major)$^b$ | 0.75 | 3.3$^{cd}$ |
| 10 (minor)$^b$ | 15.6 | 33.$^{cd}$ |
| 11 | 5.2 | 27.$^{cd}$ |
| Morphine | 3.0 | — |
| Pentazocine | 56. | 4.0 |
| | | 17.$^c$ |

$^a$hydrochloride salt
$^b$isomers of the compound of Example 7
$^c$etonitazene challenge
$^d$oral route of administration None of the compounds caused Straub tail.

The foregoing data shows that most of the compounds of the invention are more potent analgesics than pentazocine and, indeed, the compound of Example 9 is shown to have several times greater potency than morphine, which is the standard to which strong analgesics are compared. Since none of the compounds of the invention caused Straub tail, none is likely to be addictive. In addition, the results of the Straub tail antagonism test suggest that most of the compounds of the invention have very high narcotic antagonism capability. Thus, the compounds of the invention are characterized by rapid onset of action, high oral potency and the ability to alleviate deepseated pain. Furthermore, abuse liability for most of the compounds should be extremely low or nonexistent. In addition, some compounds of the invention which are pure narcotic antagonists, e.g., Example 4, will be useful for treatment of narcotic overdose.

Because of its analgetic potency, the most preferred compound of the invention for that purpose is 3-cyclopropylmethyl-5-hydroxymethyl-1,2,3,4,5,6,7,7a-octahydro-4a,7-ethanobenzofuro[3,2-e]isoquinolin-9-ol (I; R$^1$=CH$_2$-cyclo-C$_3$H$_5$, R$^2$=OH, R$^3$=CH$_2$OH, a=single bond). Other compounds may be preferred for their particular combination or profile of analgetic and narcotic antagonist effects.

Anorexia Testing Procedures

Female CF$_1$ mice, which had been fasted for 17 to 21 hours, were dosed orally with the test compound at 4, 12, 36, 108 or 324 mg/kg (five mice at each dose). One-half hour later, each mouse was transferred to an individual compartment (13.3 cm×12.7 cm×12.7 cm) with a 0.64 cm×0.64 cm wire mesh floor. Inside each compartment was a black bar (13 cm×1.2 cm×1.2 cm) in the top of which were ten spot depressions (0.8 cm diameter). Each depression contained 0.05 ml of 50% sweetened condensed milk. Thirty minutes after the mice were transferred into the compartments, the number of milk spots each mouse had consumed was counted. Fractions of spots consumed also were estimated and counted. The five mice tested at each dose could consume a maximum of fifty spots; an anorexigenic effect was considered to be obtained when fifteen or fewer spots were consumed. The doses at which an anorexigenic effect was obtained for the tested compounds are presented in Table 3.

TABLE 3

| | Anorexigenic Effect |
|---|---|
| Example | Effective Dose (mg/kg) |
| 1 | 20 |
| 2 | >324 |
| 4$^a$ | 7 |
| 6$^a$ | 46 |
| Naloxone | 4.8 |

$^a$hydrochloride salt.

From these test results, it is expected that many of the compounds of this invention will have utility as anorexia-inducing agents. Because of its anorexigenic potency, the most preferred compound of the invention for that purpose is 3-propyl-1,2,3,4,5,6,7,7a-octahydro-4a,7-ethanobenzofuro[3,2-e]isoquinolin-9-ol hydrochloride (I; R$^1$=n-Pr; R$^2$=OH; R$^3$=H; a=single bond).

UTILITY

The foregoing test results suggest that the compounds of this invention have utility as analgesics, narcotic antagonists or anorexia-inducing agents or a combination thereof. In addition, it is expected that the compounds of this invention may be useful for treating the conditions of various forms of shock, stroke and spinal cord trauma.

Analgesic and narcotic antagonist agents of this invention can be administered to treat pain or to alleviate the effect of narcotic agents by any means that produces contact of the active agent with the agent's site of action in the body of a mammal. The anorexigenic agents of this invention should be administered orally. The compounds can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon the use and known factors such as the pharmacodynamic characteristics of the particular agent, and its mode and route of administration; age, health, and weight of the recipient; nature and extent of symptoms, kind of concurrent treatment, frequency of treatment, and the effect desired. For use as an analgesic or narcotic antagonist, a daily oral dosage of active ingredient can be about 0.01 to 100 milligrams per kilogram of body weight. Ordinarily a dose of 0.05 L to 25 and preferably 0.10 to 10 milligrams per kilogram per day given in divided doses 1 to 4 times a day or in sustained release form is effective to obtain desired results. For use as an anorexigenic agent, a daily oral dose of about 1 to 100 mg/kg/day should be effective.

Dosage forms (compositions) suitable for internal administration contain from about 0.1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film-coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stablizing agents, and if necessary, buffer substances. Antioxidizing agents such as sodium bisulfite, sodium sulfite, or ascorbic acid either alone or combined are suitable stablizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, E. W. Martin, a standard reference text in this field.

Useful pharmaceutical dosage-forms for administration of the compounds of this invention can be illustrated as follows:

Capsules (Hard)

A large number of unit capsules are prepared by filling standard two-piece hard gelatin capsules each with 10 milligrams of powdered active ingredient, 215 milligrams of lactose, 24 milligrams of talc, and 6 milligrams of magnesium stearate.

Capsules (Soft)

A mixture of active ingredient in soybean oil is prepared and injected by means of a positive displacement pump into gelatin to form soft gelatin capsules containing 10 milligrams of the active ingredient. The capsules are washed in petroleum ether and dried.

Tablets

A large number of tablets are prepared by conventional procedures so that the dosage unit is 10 milligrams of active ingredient, 6 milligrams of magnesium stearate, 70 milligrams of microcrystalline cellulose, 11 milligrams of cornstarch and 315 milligrams of lactose. Appropriate coatings may be applied to increase palatability or delay absorption.

Injectable Composition

A parenteral composition suitable for administration by injection is prepared by stirring 2.0% by weight of active ingredient in 10% by volume propylene glycol and water. The solution is sterilized by filtration.

Suspension

An aqueous suspension is prepared for oral administration so that each 5 milliliters contain 2 milligrams of finely divided active ingredient, 200 milligrams of sodium carboxymethyl cellulose, 5 milligrams of sodium benzoate, 1.0 gram of sorbitol solution, U.S.P., and 0.025 milliliter of vanillin.

While the preferred embodiments of the invention are described by the above, it is to be understood that the invention is not limited to the precise embodiments herein disclosed and that the right to all changes and modifications coming within the scope of the invention as defined in the following claims is reserved.

I claim:

1. Compound of the formula:

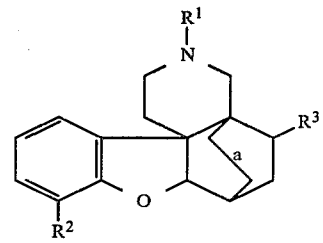

wherein, $R^1$ is selected from the group consisting of —H, $C_{1-10}$ alkyl, —$CH_2R^6$,

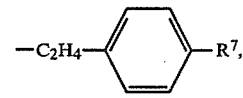

and —$(CH_2)_n CN$ in which n=1–3;

$R_2$ is selected from the group consisting of —H, —OH, $C_{1-2}$ alkoxy and $C_{2-12}$ acyloxy of an alkanoic acid;

$R^3$ is selected from the group consisting of —H, $C_{1-8}$ alkyl, and —$C(OH)(R^4)R^5$;

a is a single or double bond;

$R^4$ is selected from the group consisting of —H, and $C_{1-8}$ alkyl;

$R^5$ is selected from the group consisting of —H, $C_{1-8}$ alkyl, $C_{1-8}$ alkenyl, $C_{1-8}$ cycloalkyl, and —$CH_2)_m C_6H_5$ in which m=0–4 inclusive;

$R^6$ is selected from the group consisting of

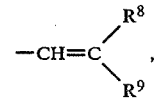

—C≡CH, $C_{3-6}$ cycloalkyl, phenyl, 2-thienyl, 2-furyl, 2-tetrahydrofuryl, methyl substituted 2-furyl and methyl substituted 2-tetrahydrofuryl;

$R^7$ is selected from the group consisting of —H, $C_{1-3}$ alkyl, —$OCH_3$, —Cl, —Br and —F; and each of $R^8$ and $R^9$ is independently selected from the group consisting of —H, —$CH_3$ and —Cl.

2. Compound of claim 1 wherein $R^1$ is cyclopropylmethyl, $R^2$ is —OH, $R^3$ is hydroxymethyl and a is a single bond.

3. Compound of claim 1 wherein $R^1$ is n-propyl, $R^2$ is —OH, $R^3$ is —H and a is a single bond.

4. Acid addition salt of the compound of claim 1.

5. Acid addition salt of the compound of claim 2.

6. Acid addition salt of the compound of claim 3.

7. Composition comprising a pharmaceutical carrier and an effective analgesic or antagonist or anorexigenic amount of a compound of any of claims 1 to 6.

8. Method for the treatment of pain and/or for alleviating the effect of a narcotic drug and/or for exerting an anorexigenic effect in a mammal comprising administering internally to the mammal an effective analgesic or antagonist or anorexigenic amount of a compound of either of claims 1 or 4.

9. Method for the treatment of pain in a mammal comprising administering internally to the mammal an effective analgesic amount of the compound of any of claims 2 or 5.

10. Method for alleviating the effect of a narcotic drug in a mammal comprising administering internally to the mammal an effective antagonist amount of a compound of any of claims 3 or 6.

11. Method for exerting an anorexigenic effect in a mammal comprising administering internally to the mammal an effective anorexigenic amount of the compound of either of claims 3 or 6.

* * * * *